(12) United States Patent
Mashiko et al.

(10) Patent No.: US 7,662,170 B2
(45) Date of Patent: Feb. 16, 2010

(54) MEDICAL NEEDLE AND CUTTING TOOL

(75) Inventors: Masaki Mashiko, Tochigi-ken (JP); Kanji Matsutani, Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 357 days.

(21) Appl. No.: 11/222,557

(22) Filed: Sep. 9, 2005

(65) Prior Publication Data

US 2006/0058843 A1    Mar. 16, 2006

(30) Foreign Application Priority Data

Sep. 13, 2004    (JP)    .............................. 2004-265387

(51) Int. Cl.
*A61B 17/06* (2006.01)
(52) U.S. Cl. ...................... 606/222; 148/206
(58) Field of Classification Search ................. 606/223, 606/222; 148/206; 359/620
See application file for complete search history.

(56) References Cited

U.S. PATENT DOCUMENTS

| 5,730,732 | A | 3/1998 | Sardelis et al. |
| 6,352,803 | B1 * | 3/2002 | Tong et al. ...................... 430/5 |
| 6,547,888 | B1 | 4/2003 | Williams et al. |
| 6,674,577 | B2 * | 1/2004 | Slashchenko ............... 359/620 |

FOREIGN PATENT DOCUMENTS

| CH | 621476 | A * | 2/1981 |
| DE | 3841443 | C1 * | 1/1990 |
| EP | 621 476 | A | 2/1981 |
| EP | 3841 443 | C1 | 1/1990 |
| EP | 0 726 065 | A | 8/1996 |
| EP | 1 078 602 | A | 2/2001 |

OTHER PUBLICATIONS

Wikipedia (http://en.wikipedia.org/wiki/Austenitic_stainless_steel.*

* cited by examiner

*Primary Examiner*—Roy King
*Assistant Examiner*—Weiping Zhu
(74) *Attorney, Agent, or Firm*—Townsend & Banta (57) ABSTRACT

A medical needle and the like that has small resistance when piercing, scraping or incising the body tissue, that is not easily bent and that reduces the reflection of the illumination as much as possible when in surgery performed under scope is provided. The medical needle and the like has a hardened layer, in which a carbon atom is penetrated, of a depth of 5 micrometers to 70 micrometers provided on a parent material surface of a fiber shape structure having an austenite stainless steel containing 1% to 6% of molybdenum or 13% to 25% of chromium. Further, after the hardened layer is provided, one part of the hardened layer is removed. Further, the dark layer is formed on the outer most surface of the hardened layer to provide a non-reflective surface.

2 Claims, 8 Drawing Sheets

MEDICAL NEEDLE AND CUTTING TOOL

BACKGROUND OF THE INVENTION

The present invention relates to a medical needle or a cutting tool that does not produce rust and that provides high hardness as well as difficult bending property, and that further has non-reflectivity.

The medical needle includes, a suture needle used for suturing the affected area that has been incised or a needle used for blood drawing or fluid infusion, a reamer or a file used for performing root canal forming in dental treatment and the like. The medical cutting tool includes a surgical knife or a knife used when incising the affected area. Thus, the medical needle and the cutting tool have suitable shape in accordance with the intended use.

All of the above mentioned medical needle and the cutting tool have a function of piercing directly through the body tissue and passing the suture thread, or a function of scraping the structure of the teeth or a function of incising the body tissue. In such medical needle or the cutting tool, a force acts in a bending direction when performing the intended task, or a resistance when piercing through the body tissue, a resistance when scraping, or a resistance when cutting may act.

The treatment instrument for the root canal forming in the dental treatment is often required to scrape the hard layer of the surface of the teeth, and thus needs to have high hardness. On the other hand, when broken by an obstacle while working in the root canal forming, the task of removing the broken distal end portion is not easy. That is, the dental treatment instrument must have both a hard cutting blade and a high-level of difficult bending property. Since such medical needle or cutting tool directly contacts the body tissue, it is configured using a material that has no adverse effect on the body tissue.

Thus, in actual condition, the needle or tool that is not easily bent during use and has small resistance is continuously being developed in each manufacturing corporations.

A material having high hardness must be used to reduce the resistance when piercing, scraping or incising the body tissue, and to produce high resistance with respect to the bending force, and hardening processed steel or martensitic stainless steel is commonly used for such material. However, in the medical needle or cutting tool that uses such material, occurrence of rust in the circulation step is difficult to avoid.

Thus, the applicant of the present invention has developed a medical needle that has high hardness obtained through work hardening by performing cold pulling work on the austenite stainless steel, and that achieves difficult bending property by having fiber shape structure which is extended from the granulated austenite structure (refer to e.g. Japanese Patent Application Publication (JP-B) No. 1-11084). The medical needle obtained through such technique has advantages in that rust is not produced, sharpness of the cutting blade is ensured by having high hardness, and further, difficult bending property is obtained since the structure is extended into a fiber shape.

Since hardness due to thermal treatment cannot be expected in the austenite stainless steel, work hardness involved in cool working must be expected, as in the technique of JP-B No. 1-11084. Therefore, since the process for obtaining hardness is only through cold working, the types of products that can be applied to are extremely limited, and in order to overcome such problem, a technique of forming a hardened layer by performing carburization process on the austenite stainless steel has been developed (refer to e.g., Japanese Patent Application Laid-Open (JP-A) No. 9-268354).

SUMMARY OF THE INVENTION

When the medical needle or the cutting tool is configured by fiber shape structure of the austenite stainless steel, it is superior to any that is configured by any other stainless steel with regards to the difficult bending property due to high toughness, but is inferior with regards to the bending strength. The hardness thus must be enhanced by performing the technique of JP-B No. 1-11084. In this case, the working conditions of the working rate and the like until the hardness necessary for the medical needle or the cutting tool is obtained must be strictly managed, cool working with extremely high precision must be performed, and the management of the work procedures or the management of the environment becomes complex.

In the technique of JP-A No. 9-268354, on the other hand, the hardness may be increased by forming the carburized layer on the surface of the product, but when applied to the product of long rod shape where the bending force is acted, the problem of difficult bending property cannot be solved.

Further, in recent medical treatment, delicate surgery such as brain surgery, ophthalmic surgery or root canal formation and the like is being performed. In such delicate surgery, generally, the operating field is monitored with a microscope or an endoscope while incising or suturing the affected area or performing root canal formation and the like. In surgery under such scope, the illumination irradiating the operating field is reflected by the medical needle or the cutting tool, thereby giving great fatigue to the physicians.

The present invention aims to provide a medical needle or a cutting tool that has high resistance to bending and that is not easily bent, that has small resistance when piercing, scraping or incising the body tissue, and that reduces the reflection of the illumination as much as possible even in the surgery under scope.

In the medical needle or the cutting tool according to the present invention for solving the above problem, a hardened layer, in which the carbon atom is penetrated, with a depth of 5 micrometer to 70 micrometer is formed on the parent material surface of fiber shape structure of the austenite stainless steel containing molybdenum in a range of 1% to 6% or containing chromium of between 13% to 25%.

In the second medical needle or the cutting tool according to the present invention, after the hardened layer, in which the carbon atom is penetrated, with a depth of 5 micrometer to 70 micrometer is formed on the parent material surface of the austenite stainless steel containing molybdenum in a range of 1% to 6% or containing chromium of between 13% to 25%, one part of the hardened layer is removed.

Further, in the third medical needle or the cutting tool according to the present invention, the hardened layer, in which the carbon atom is penetrated, is formed on the parent material surface of the austenite stainless steel containing molybdenum in a range of 1% to 6% or containing chromium of between 13% to 25%, and a dark layer is formed on the outer most surface of the hardened layer to provide a non-reflective surface.

Further, in the fourth medical needle or the cutting tool according to the present invention, more hardened layer is removed towards the needle point or the blade point of the medical needle or the cutting tool.

Moreover, in the fifth medical needle or the cutting tool according to the present invention, the structure of the austenite stainless steel is a fiber shape structure.

Further, in the sixth medical needle or the cutting tool according to the present invention, a silicon coating is formed on the dark layer.

In the first medical needle or the cutting took (hereinafter referred to as "medical needle and the like") according to the present invention, the hardened layer of 5 micrometer (μm) to 70 μm is provided on the surface of the parent material in which the structure of the austenite stainless steel is extended into a fiber shape, and thus, a cutting blade that is strong against bending and that has high hardness on the surface is formed, thereby reducing the resistance when piercing the body tissue, the resistance when scraping or the resistance when incising. Since the parent material has fiber shape structure, a medical needle and the like that provides difficult bending property, is strong against bending and is not easily bent, the properties not conventionally realized, can be provided.

In particular, due to austenite stainless steel, rust is not produced, and the body tissue is not adversely affected even when the medical needle and the like directly contact the body tissue.

In the second medical needle and the like, after the hardened layer is formed by carburizing the parent material surface, one part of the hardened layer is removed to eliminate the portion that has become fragile on the outer most surface due to carburization. Thus, the easy bending property due to fragility is resolved and can withstand a plurality of usages, and a surface having a stable hardness is formed. Further, in the fourth medical needle and the like, more hardened layer is removed towards the needle point or the blade point of the medical needle or the cutting tool, thereby suppressing the influence of fragility of the distal end portion. In the fifth medical needle and the like, the structure of the austenite stainless steel is made into a fiber shape structure, thereby exhibiting bending strength and difficult bending property.

In the third medical needle and the like, the dark layer is formed on the outer most surface of the hardened layer provided on the parent material surface to provide the non-reflective surface, so that even when strong illumination is irradiated on the operating field in surgery under scope using microscope or endoscope, the illumination light is not reflected towards the physician side, thereby suppressing the fatigue of the physician. Further, in the sixth medical needle and the like, a silicon layer is formed on the dark layer thereby enhancing corrosion resistance (corrosion-inhibiting performance).

BRIEF DESCRIPTION OF THE DRAWINGS

FIG. 1 is a view explaining an example of a suture needle serving as a medical needle and the like;

FIG. 2 is a view explaining another example of a suture needle serving as the medical needle and the like;

FIG. 5 is a view explaining an example of a knife serving as the medical needle and the like;

FIG. 6 is a view explaining another example of a knife serving as the medical needle and the like;

FIG. 7 is a view explaining an example of a Pesso reamer serving as the medical needle and the like; and FIG. 8 is a view explaining an example of a file serving as the medical needle and the like.

DETAILED DESCRIPTION OF THE PREFERRED EMBODIMENTS

The preferred embodiments of the medical needle and the like according to the present invention will now be described. The medical needle and the like of the present invention has a sharp needle point that pierces the body tissue and a cutting blade that incises or scrapes the body tissue, which medical needle and the like has the sharpness of the needle point or the cutting blade enhanced by increasing the hardness of the surface. Thus the piercing resistance when piercing the body tissue is reduced, and the resistance when incising or scraping the body tissue is reduced. In particular, when the hardness of the surface is increased, piercing ability and sharpness are maintained irrespective of the usages over a plurality of times, and thus is a user friendly medical tool and the like.

Further, non-reflectivity can be exercised by forming a dark layer on the outermost surface, which eliminates or reduces the reflected light thereby alleviating the fatigue of the physicians even when illumination light for the operating field is irradiated on the medical needle and the like when performing delicate surgery using microscope or endoscope.

The material used for the medical needle and the like of the present invention is an austenite stainless steel containing molybdenum in the range of 1% to 6%, or containing chromium in the range of 13% to 25%. That is, the material of the medical needle and the like only needs to be an austenite stainless steel containing molybdenum or chromium in the above range, and does not limit the content material of the metal other than the above metals. However, it is preferably a standardized product standardized in JIS G 4304-4309.

Preferably, the austenite stainless steel serving as the material of the medical needle and the like is easily available from the general market, and in terms thereof, is preferably SUS303, SUS304 and the like. Such austenite stainless steel does not have the possibility of producing rust over a long period of time, and a fair surface is always maintained.

The medical needle and the like of the present invention has an extremely small dimension compared to the usual mechanical components (e.g., in case of medical suture needle, the thickness at the thickest part is in the range of about 0.07 mm to about 1.4 mm). Since the thickness of the product is extremely thin, the wire of the austenite stainless steel having a wire diameter corresponding to the thickness of the product in advance is preferably used for the material.

The first and the fifth medical needle according to the present invention uses a material in which the structure of the austenite stainless steel is extended into a fiber shape by performing cool pulling work with the wire of the austenite stainless steel corresponding to the thickness of the target medical needle and the like.

In this case, the working conditions in cool pulling work of the austenite stainless steel are not particularly limited, and that in which the structure is extended into a fiber shape and the hardness is increased by cool pulling work at a pre-set regressive rate can be used. Thus, by performing cool pulling work on the austenite stainless steel and extending the structure into a fiber shape, the raw material that has a pre-set thickness and a predetermined hardness, and that has difficult bending property is obtained.

In the first and fifth medical needle and the like, when performing cool pulling work on the austenite stainless steel to extend the structure into a fiber shape, only the extension of the structure must be realized and the hardness of the raw material does not need to be limited and provided. That is, the hardness of the surface is achieved by providing a hardened layer (carburized layer), in which the carbon atom is penetrated, of a depth of 5 μm to 70 μm on the parent material surface of the fiber shape structure.

Further, in the second to the fourth and the sixth medical needles and the like, the material simply needs to be an austenite stainless steel, and does not limit whether the structure is extended to a fiber shape or not. Even with the second to the fourth and the sixth medical needle and the like, the hardness of the austenite stainless steel is achieved by providing a hardened layer (carburized layer), in which the carbon atom is penetrated, of a depth of 5 μm to 70 μm on the parent material surface.

Means for forming the hardened layer in which the carbon atom is penetrated on the parent material surface of the austenite stainless steel is not particularly limited, but the formation of the hardened layer is preferably performed after being worked into the shape or dimension of the medical needle and the like set in advance. Therefore, by realizing the dimension or shape in advance, the hardened layer can be formed over the entire needle point or the cutting blade formed in the medical needle, and the medical needle and the like having a uniform hardness distribution can be obtained.

An example of a carburization process of when forming the hardened layer made of carburized layer includes the following method. The fluorine compound gas (gas containing fluorine F in the molecule) is solely or mixed with a plurality of types before or simultaneously with the carburization process, and the fluorine process is performed under the fluorine gas atmosphere diluted with nitrogen gas. The fluorine process is maintained at a temperature of 400° C. to 500° C. and the target medical needle and like is placed in the oven of the fluorine gas atmosphere and maintained therein over a predetermined time.

Next, the oven is changed from the fluorine gas atmosphere to the carburizing gas atmosphere containing carbon monoxide and hydrogen, and the oven temperature is set to 400° C. to 500° C. and maintained over a predetermined time, thereby allowing the carburized layer that becomes the hardened layer in which the carbon atom is penetrated to be formed on the surface of the medical needle made of austenite stainless steel. The depth of the hardened layer is proportional to the time that has elapsed in the carburizing gas atmosphere. Therefore, it is preferably placed in the oven over a time corresponding to the depth of the hardened layer necessary for the medical needle.

When the oven temperature is made higher than 500° C. in performing fluorine process and carburization process on the austenite stainless steel having a structure extended into a fiber shape, the fiber shape structure may recrystallize into the granulated austenite structure. Thus, in first aspect of the invention, the oven temperature must be maintained to equal to or lower than 500° C.

As noted above, the medical needle or the instrument for root canal forming has different thickness depending on the size, and is in a range of about 0.07 mm to about 1.4 mm. Thus, the depth of the hardened layer cannot be uniformly defined, and the suitable depth (shallow for narrow ones and deep for thicker ones) is set in accordance with the thickness. That is, the deeper the depth of the hardened layer, a stable hardness is provided and a stable piercing and scraping or incision ability is provided even over a plurality of usages. In the medical needle and the like having a thin thickness, however, if the hardened layer is made deep with respect to the thickness, it may be easily bent when the bending force is applied.

For example, when the medical needle is the instrument for root canal forming, with respect to the narrowest #06, the thickness of the pointed portion becomes about 40 μm. The depth of the hardened layer of 5 μm is enough for such thickness.

In the second, the fourth, and the fifth medical needle and the like according to the present invention, one part of the hardened layer is removed after arranging the hardened layer in which the carbon atom is penetrated on the parent material surface of the austenite stainless steel. In particular, by removing a part of the surface of the hardened layer, the fragile layer produced in the carburizing process can be eliminated. Thus, when piercing, scraping, or incising the body tissue with the medical needle and the like, the easy bending of the medical needle and the like can be improved.

Further, in the third and the sixth medical needle and the like according to the present invention, the non-reflective surface is obtained by forming the dark layer on the outer most surface of the hardened layer formed on the surface of the parent material of the austenite stainless steel. The dark layer is specifically, an iron oxide layer, a chromium oxide layer, a chromium carbide layer and the like. The method of forming the dark layer on the outer most surface of the hardened layer is not particularly limited, and can be formed by adjusting the atmosphere, the temperature and the like in the carburizing process, or performing the carburizing process leaving a small amount of oxygen in the carburizing atmosphere.

Each medical needle and the like according to the present invention obtain high hardness since the hardened layer made of carburized layer is formed on the surface. In such medical needle and the like, the intended task can be performed with the hardened layer in the exposed state, but a silicon layer is preferably formed on the outer most surface. In particular, when the medical needle and the like is a suture needle that passes through the body tissue or a cutting tool that incises the body tissue, the contact friction produced between the suture needle, or the cutting tool and the body tissue is alleviated by forming the silicon layer, thereby reducing the resistance.

In particular, if the silicon layer is formed after wiping the chromium carbide layer of the outer most surface of the dark layer in the third medical needle and the like, corrosion resistance is enhanced. In such case, the silicon layer can be strongly secured by forming the silicon layer after roughening the surface through light acid cleaning process.

In each medical needle and the like, when the hardened layer made of carburized layer is formed on the surface of the parent material, occurrence of fragility is difficult to avoid. In particular, since the needle point or the distal end portion of the cutting blade and the like serving as the distal end portion of the suture needle or the dental treatment instrument is formed so as to be extremely narrow or thin, force is intensively applied and thus is easily subjected to fragility. Thus, in order to suppress the influence of fragility, the depth of the hardened layer is limited. The ratio of the hardened layer with respect to the parent material is not particularly limited, but in the experiments performed by the inventors of the present application, the ratio is preferably 1 to 9 in the case of the suture needle.

Embodiment 1

Figure 1:
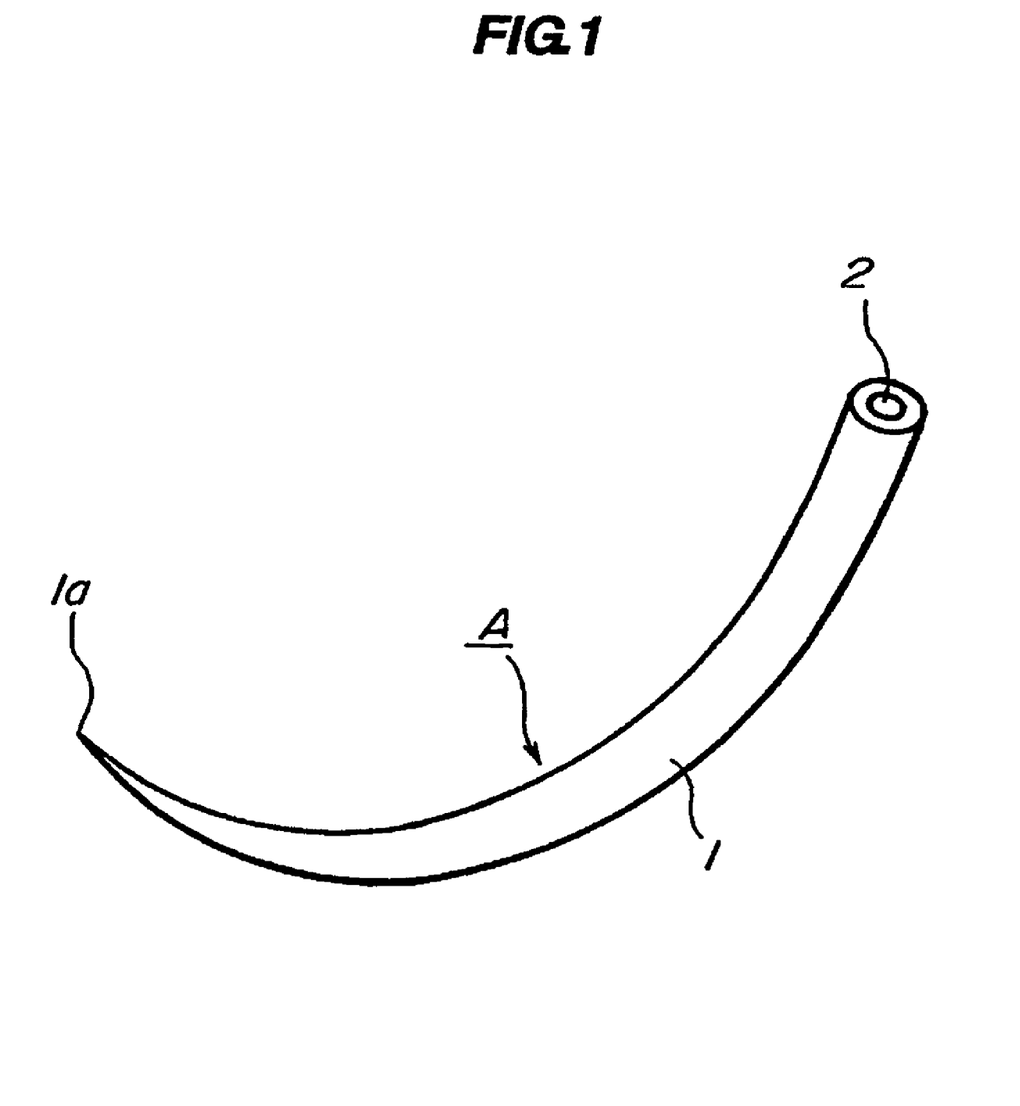
Figure 2:
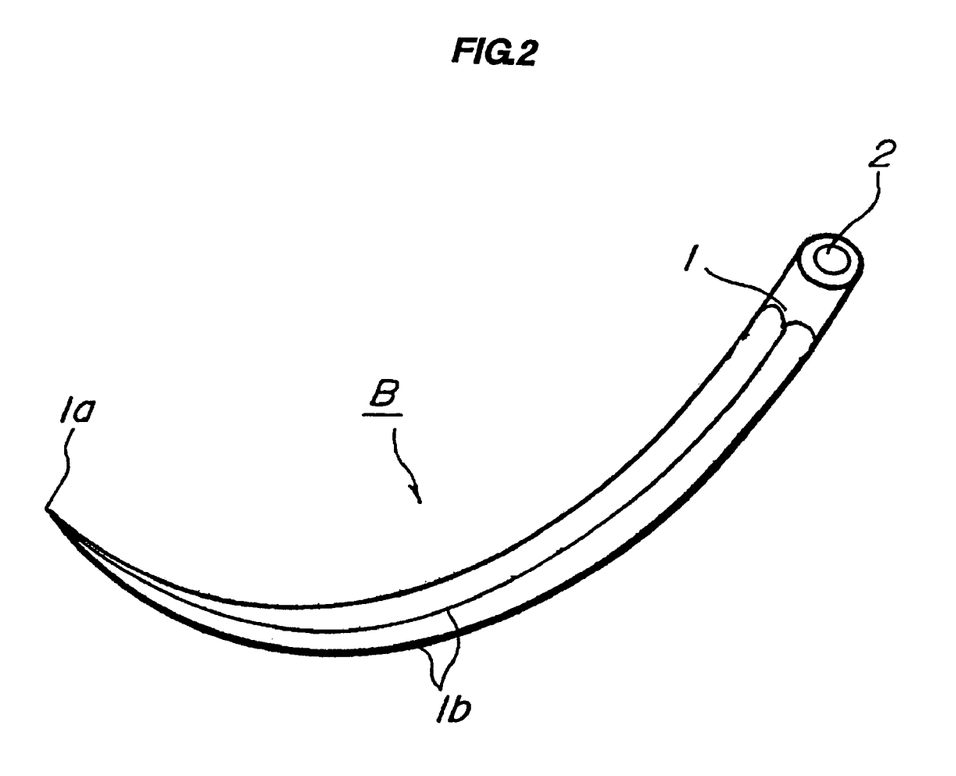
Figure 3:
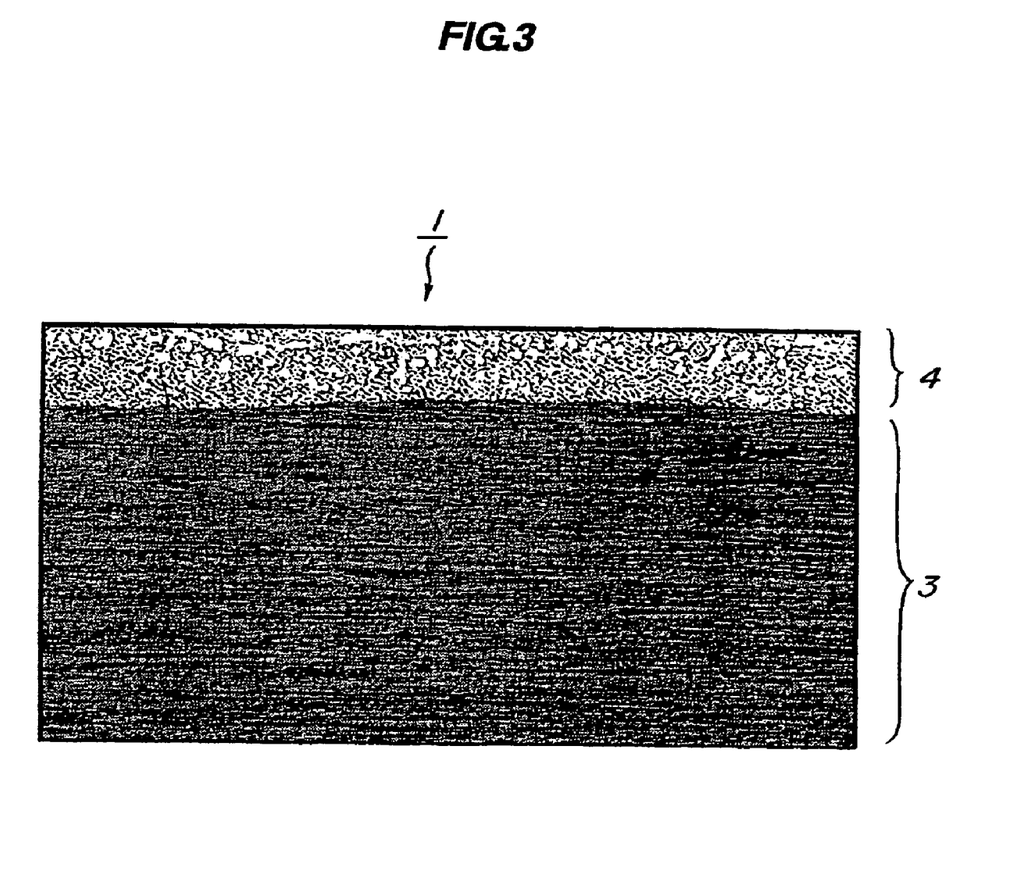
FIG. 3 is a view explaining an example of a fiber shape structure obtained by performing cool pulling work on the austenite stainless steel.
Figure 4:
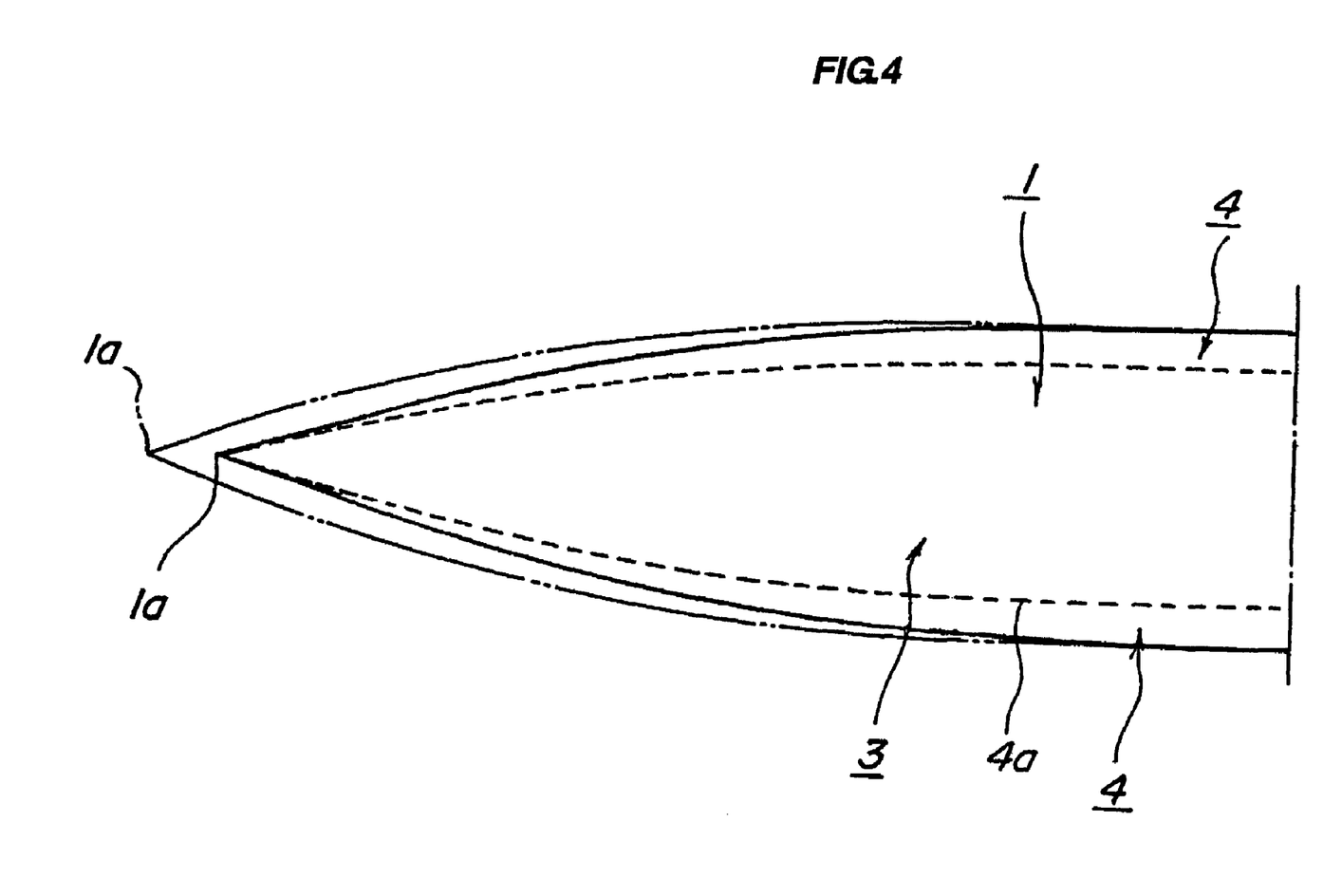
FIG. 4 is a view explaining a preferred example of a distal end portion of the suture needle.

The first embodiment of the medical needle and the like will now be explained using the figures. FIG. 1 is a view explaining an example of a suture needle serving as the medical needle and the like. FIG. 2 is a view explaining another example of the suture needle serving as the medical needle and the like. FIG. 3 is a view explaining an example of a fiber shape structure obtained through cool pulling work of the austenite stainless steel. FIG. 4 is a view explaining a preferred example of the distal end portion of the suture needle.

In the present embodiment, the medical needle and the like is formed as a suture needle A shown in FIG. 1 and suture needle B shown in FIG. 2. The suture needle A has the cross section of the body part 1 formed into a circular shape, a sharp needle point 1a is formed at the distal end, and a hole 2 through which the suture thread (not shown) is inserted and bonded is formed at the rear end face. The suture needle A pierces the body tissue with the needle point 1a and passes through the body tissue so as to push open the body tissue with the body part 1.

The suture needle B has the cross section of the body part 1 formed into a polygon (e.g., triangle or pentagon shape and the like), and the ridge line set in advance is formed as a cutting blade 1b for cutting open the body tissue. The suture needle B pierces the body tissue with the needle point 1a and passes therethrough so as to open up the body tissue with the cutting blade 1b.

The suture needle A, B has a body part 1 in which the structure that was granulated in the initial state is extended into a fiber shape by performing cool pulling work on the austenite stainless steel at a pre-set regressive rate (refer to FIG. 3). In such body part 1, the fiber shape structure has high resistance to bendability, and provides difficult bending property against the bending force that acts when passing the body tissue in suture surgery.

As shown in FIG. 3, the hardened layer 4 in which the carbon atom is penetrated is formed on the surface of the fiber shape structure 3, the hardened layer 4 allowing the hardness necessary for suture needles A, B to be provided. In particular, high hardness is not required for the suture needle A as it does not have a cutting blade, and thus the depth of the hardened layer 4 is made shallow. Further, in the suture needle B, the depth of the hardened layer 4 is made deep to ensure the sharpness of the cutting blade 1 even when suturing over a plurality of times.

The procedures for configuring the suture needle A, for example, will now be briefly explained. First, the material (wire of the austenite stainless steel subjected to cool pulling work) corresponding to the thickness of the body part 1 of the suture needle A is selected and cut in correspondence to the length of the suture needle A to form the raw material. The raw material is grinded into a tapered shape to form the needle point 1a on one end.

The intermediate assembly of the suture needle A formed as above is inserted into an oven of fluorine gas atmosphere and the fluorine process is performed, and subsequently, maintained in the oven of the carburizing gas atmosphere over a predetermined time to form the hardened layer 4 on the surface of the fiber shape parent material. Next, a hole 2 is formed on the other end, and thereafter, a bending work is performed to bend to a predetermined curve so as to obtain the shape of the suture needle A. The suture needle A is thereby obtained.

When configuring the suture needle B, the raw material is press worked to form a target cross sectional shape, and subsequently, the surface is grinded to form the cutting blade 1b. Thereafter, the intermediate assembly is subjected to the fluorine process and the carburizing process, and curved through a predetermined bending work to obtain the shape of the suture needle B. The suture needle B is thereby obtained.

The suture needle A, B, obtained as above, has the hardened layer 4 formed uniformly over the entire surface, and thus the needle point 1a has both high hardness and fragility, and thus the needle point 1a may chip when piercing the body tissue. Thus, the hardened layer 4 at the needle point 1a (distal end portion of chain double-dashed line) after being subjected to the carburizing process is preferably removed with means such as buff polishing and the like to expose the fiber shape structure, so that the needle point 1a (distal end portion of solid line) that does not easily break is formed, as shown in FIG. 4. In particular, in removing, the ratio of the thickness in the traverse direction of the hardened layer 4 and the fiber shape structure 3 is preferably always 1 to 9 from the body part towards the needle point 1a.

The needle point 1a formed by removing the hardened layer 4 is preferably a point where the boundary line 4a of the hardened layer 4 and the fiber shape structure 3 coincide. In forming such needle point 1a, the hardened layer 4 immediately continues from the needle point 1a, and the fiber shape structure 3 that provides difficult bending property is formed at the center and the hardened layer 4 having high hardness is formed surrounding the fiber shape structure 3.

When manufacturing a plurality of suture needles A, B, performing the work so as to accurately coincide the needle point 1a with the boundary line of the hardened layer 4 and the fiber shape structure 3 may cause problems regarding cost. However, even if the needle point 1a enters the fiber shape structure 3, it can, preferably, smoothly pierce through the body tissue as the suture needle A, B.

Further, after forming the hardened layer 4 on the parent material surface of the suture needle A, one part of the hardened layer 4 may be removed by performing acid cleaning process or chemical polishing process. In this case, the fragile layer at the surface of the hardened layer 4 is removed, and suture needle A having a stable hardness is formed, as described above.

Embodiment 2

Figure 5:
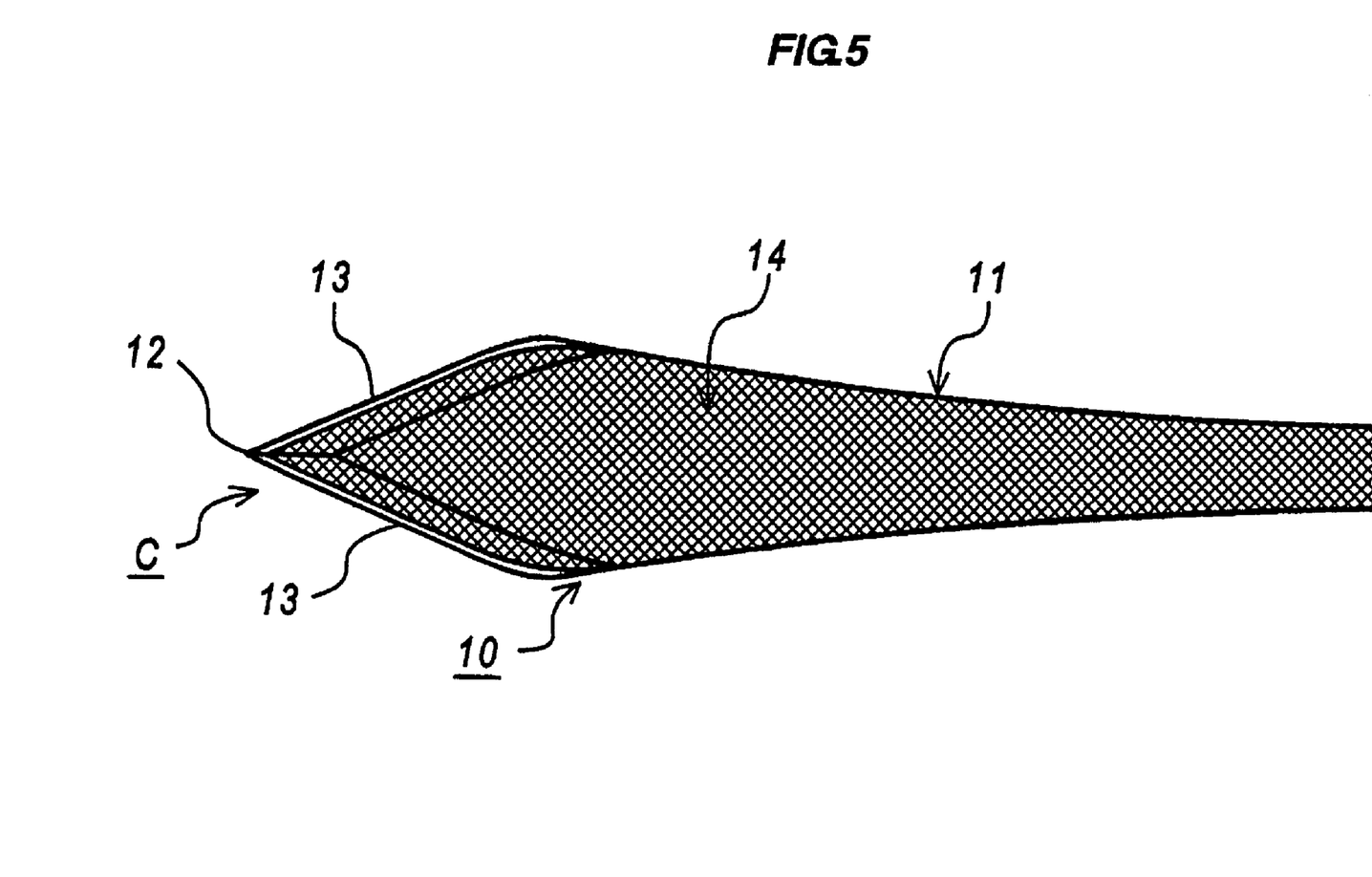
Figure 6:
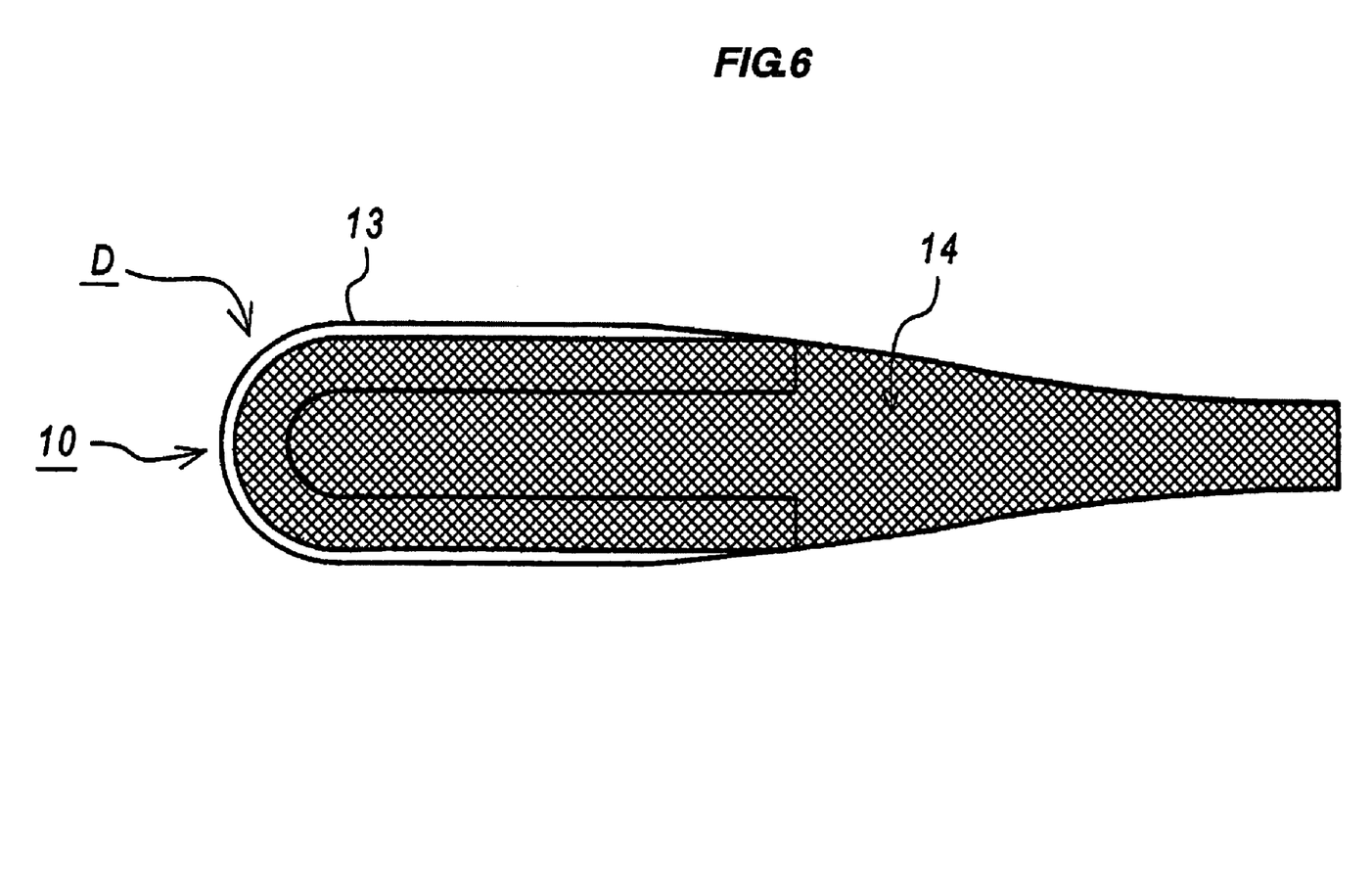

A second embodiment of the medical needle and the like will now be described with reference to the figures. FIG. 5 is a view explaining an example of a knife serving as the medical needle and the like. FIG. 6 is a view explaining another example of a knife serving as the medical needle and the like.

The knife C shown in FIG. 5 has a blade part 10 and a shank 11 continuously formed on the blade part 10. The distal end of the knife C is formed as a sharp point 12, and a cutting blade 13 is formed along the outer edges of both sides of the blade part 10 from the point 12. The dark layer 14 is formed on the surface of the knife C, and non-reflectivity is provided by the dark layer 14.

The knife D shown in FIG. 6 differs from the knife C in that the distal end portion is formed into a curved shape, but other configurations are configured the same way as the above described knife C.

In knife C, D, the material used is the austenite stainless steel, which material may have fiber shape structure or may still have granulated structure. For instance, if the material is a wire having a structure extended into a fiber shape, the wire in which the above wire is cut in correspondence to the length of the knives C, D is formed, and one end of such wire is press worked and molded into the shape of the knife C or D, thereby forming the intermediate assembly.

Thereafter, the carburizing process is performed after the intermediate assembly is grind worked to form the cutting blade 13, similar to the above mentioned first embodiment, and the hardened layer is formed on the surface of the fiber parent material. The knife C, D is thereby configured.

Even when the austenite stainless steel that does not have a structure extended into a fiber shape is used, similar to the above, press work is performed on one end of the wire cut to a predetermined length to mold into the shape of the knives C, D and the cutting blade 13 is formed, and subsequently, fluorine process and carburizing process are performed to configure the knife C, D.

The knife C, D obtained as above is formed with the cutting blade 13 having high hardness along the outer edge. Thus, it can be used as a general surgical knife. However, when using in brain surgery or ophthalmic surgery, the cutting blade 13 is preferably formed by grinding along the outer edge in the knives C, D formed with the hardened layer 4 through carburizing process and removing one part of the hardened layer 4. Thus, in the knife C, D in which one part of the hardened layer 4 is removed, a smooth incision can be realized when performing delicate surgery.

In the present embodiment, the dark layer 14 is formed on the knife C, D formed with the hardened layer on the surface as mentioned above to provide non-reflectivity. When forming the dark layer 14, carburizing process is performed leaving a small amount of oxygen in the carburizing atmosphere.

Embodiment 3

Figure 7:
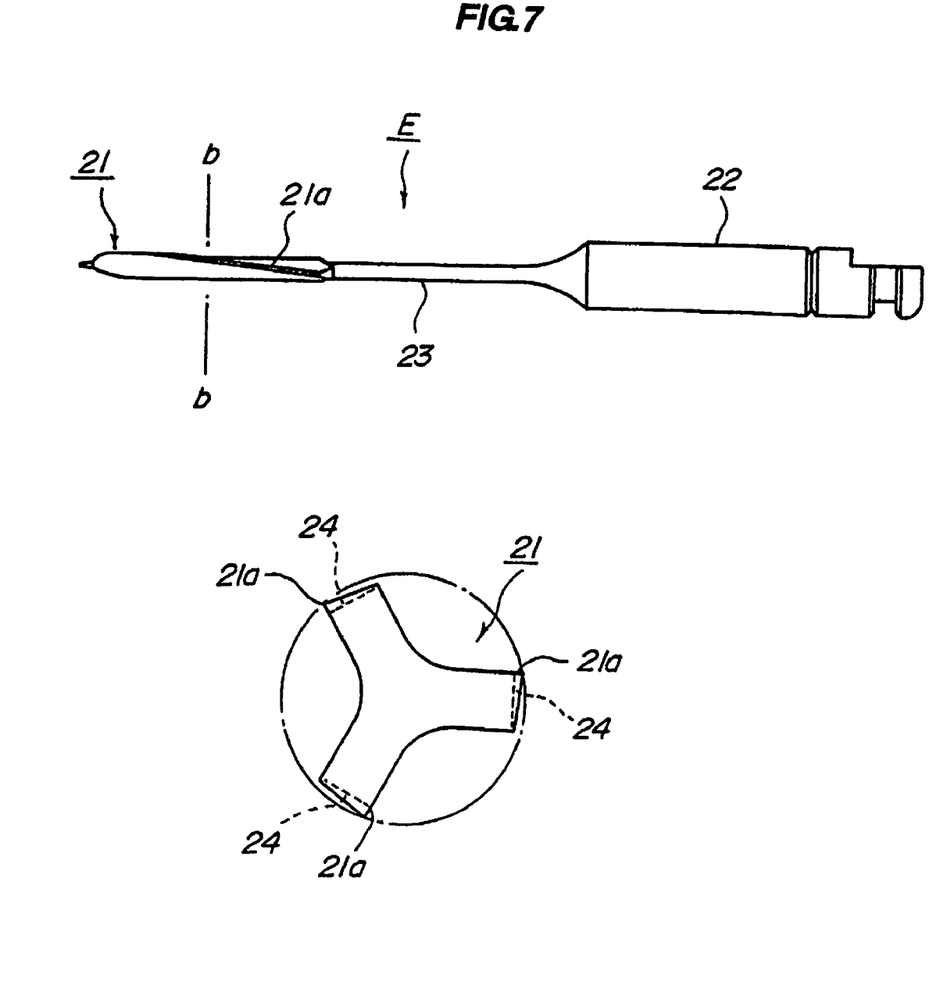

The third embodiment of the medical needle and the like will now be explained using the figures. FIG. 7 is a view explaining an example of a Pesso reamer that is a dental treatment instrument serving as the medical needle and the like. The Pesso reamer E shown in the figure is an instrument for grinding a layer having slightly high hardness such as an ivory or calcified root canal wall formed on the surface of the teeth, and is operated by being mounted on a rotating drive device called a hand piece.

The Pesso reamer E is configured by including a cutting blade part 21 formed on one end side, a shank 22 formed on the other end side and grasped by a chuck of the hand piece, and a neck part 23 formed between the cutting blade part 21 and the shank 22. The neck part 23 has a function of serving as a fuse that breaks with a twisting force and/or a bending force acting on the Pesso reamer E when some kind of problem occurs in scraping the teeth.

The cutting blade part 21 has a plurality of (three in the present embodiment) cutting blades 21a formed with a twisting angle set in advance. The cutting face and the flank of each cutting blade 21 is formed with a hardened layer 24 made of carburized layer, and the center portion is configured with the fiber shape structure obtained by performing cool pulling work on the austenite stainless steel or the granulated austenite structure that is not performed with cool pulling work.

The procedures for configuring the Pesso reamer E as above will now be simply explained. First, a predetermined work is performed on a raw material in which the wire of the austenite stainless steel having the fiber shape structure or the granulated structure is cut to a length corresponding to the length of the intended Pesso reamer E to form the cutting blade part 21 into a straight shape (state in which a plurality of cutting blades 21a is not formed), the shank 22, and the neck part 23 are formed, and the fluorine process and the carburizing process are performed in such state to form the hardened layer 24. Here, the outer peripheral surface of the cutting blade part 21 in the non-worked state is formed with the hardened layer 24 in a uniform depth.

Next, grinding is performed on the cutting blade part 21 to form a plurality of cutting blades 21a. Through such work, the cutting blade part 21 is formed with a plurality of cutting blades 21a in which each of the cutting face and the flank is configured by the hardened layer 24. Therefore, the cutting blade 21a is not formed with the hardened layer 24 across the entire surface, and the portion excluding one part of the cutting face and the flank is configured by the austenite structure extended into the fiber shape that is not easily bent or granulated austenite structure. Thus Pesso reamer E that provides high grinding ability and that is not easily bent is thereby achieved. In particular, when the portion excluding one part of the cutting face and the flank is the austenite structure extended into the fiber shape, high strength is provided with respect to the bend, and the neck part 23 is flexibly bent to allow satisfactory treatment.

When configuring the Pesso reamer E, the order of steps of fluorine process and the carburizing process is not limited to the above mentioned orders, and the fluorine process and the carburizing process may be performed after a plurality of cutting blades 21a is formed on the cutting blade part 21 in advance.

Embodiment 4

Figure 8:
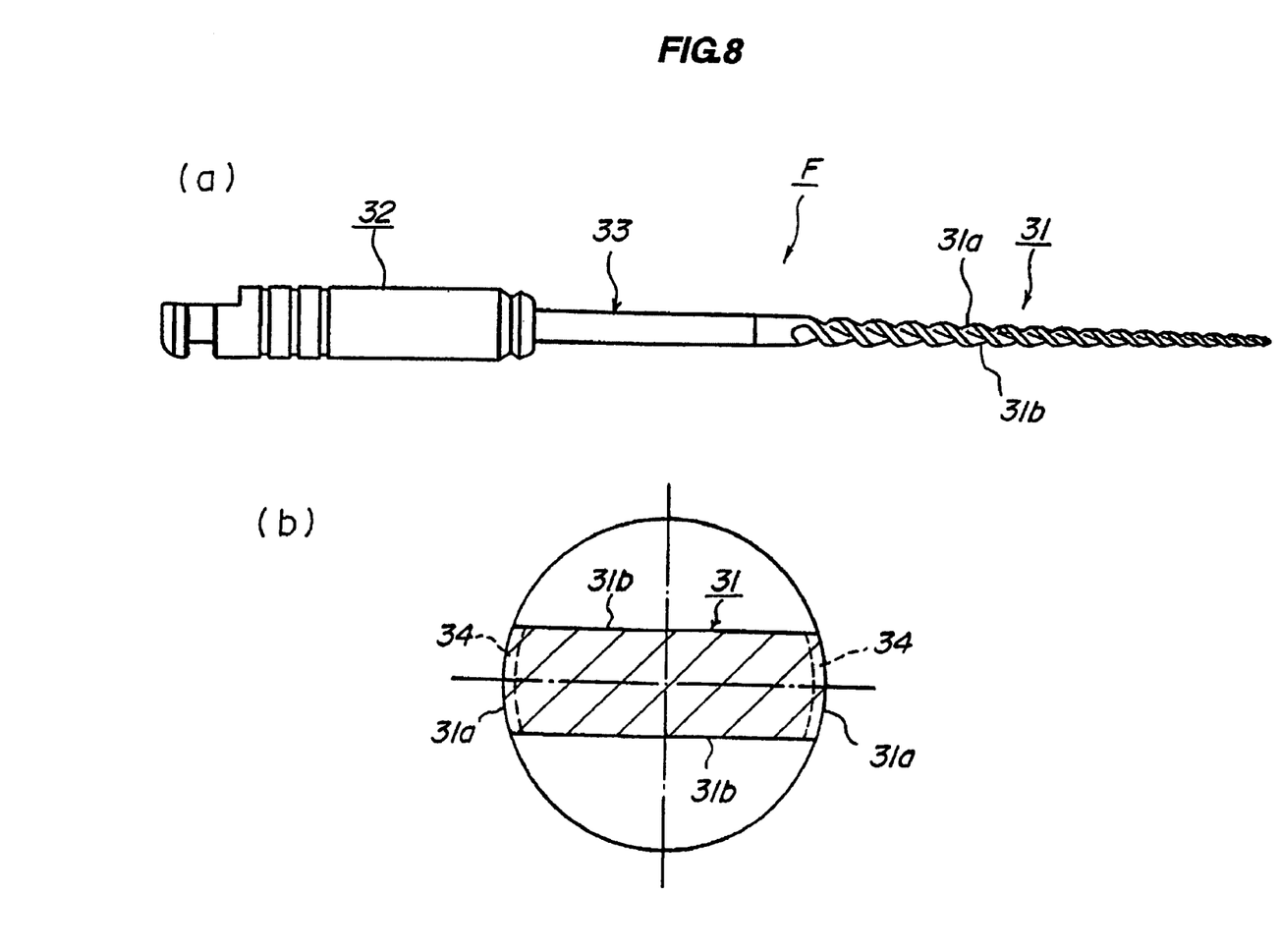

The fourth embodiment of the medical needle and the like will now be explained. FIG. 8 is a view explaining an example of a file that is a dental treatment instrument serving as the medical needle and the like. The file F shown in the figure is an instrument for grinding the surface of the calcified root canal wall and forming the root canal, and is operated by being mounted on a rotating drive device called a hand piece.

The file F performs the formation of the root canal and at the same time has a function of eliminating the cutting waste to the outside and eliminating the content in the root canal to the outside. In particular, the root canal is gradually thinned towards the root point and is curved, and since such curved shape differs greatly among individuals, the file F is required to grind the root canal wall while flexibly following the curve of the root canal. Thus, the file F needs a property having both high grinding performance and sufficient flexibility.

The file F is configured by including a work part 31 which is entirely formed by grinding the tapered raw material, a shank 32 grasped by the chuck of the hand piece (not shown), and a body part 33 secured to the shank 32 formed continuously from the work part 31.

A hardened layer 34 made of carburized layer is formed on the cutting face and the flank of the cutting blade 31a, which hardened layer 34 allows the cutting blade 31a to exhibit high hardness. The center portion is configured by the fiber shape structure obtained by performing cool pulling work on the austenite stainless steel or the granulated austenite structure that is not performed with cool pulling work.

The procedures for configuring the file F will now be briefly explained. First, the raw material in which the wire of the austenite stainless steel having the fiber shape structure that is performed with cool pulling work or wire having granulated austenite structure that is not performed with cool pulling work is cut in correspondence to the length of the target file F, and the center-less work is performed on the raw material to form the portion corresponding to the work part 31 into a tapered shape, thereby configuring the intermediate assembly.

The fluorine process and carburizing process are performed on the intermediate assembly to form the hardened layer 34 on the entire surface, and thereafter, the tapered work part 31 is grinded into a spiral shape so as to have a flat cross section leaving the hardened layer 34 on the cutting face and the flank of the cutting blade part 31a. After forming the spiral shaped work part 31, the body part 33 is coupled to the shank 32. The file F is thereby obtained.

The order of steps of performing the fluorine process and the carburizing process is not limited to the above, and the hardened layer 34 may of course be formed on the cutting blade 31*a* through the above processes after forming the spiral shaped work part 31.

In this case, the work part 31 may be configured by forming the cutting blade 31*a* into an angular part by grinding the opposing surface of the portion formed into a tapered shape in advance to form a flat cross section, and then forming the spiral shaped cutting blade 31*a* and the spiral shaped groove 31*b* by twisting the above portion with a twisting angle set in advance. The work part 31, having the material of the flat cross section twisted, achieves flexible following along the curve of the root canal when forming the root canal.

The order of steps of performing the fluorine process and the carburizing process is not limited, but when the fluorine process and the carburizing process are performed after the twisting work, the twisted shape formed in the twisting work can be fixed by the hardened layer 34. Thus, the problem existing from the prior art in that the twist tends to return while using is avoided. Therefore, the fluorine process and the carburizing process are preferably post-processes of the twisting work.

In the root canal treatment instrument represented by the file F, it is required to flexibly follow the curve of the root canal. That is, in the prior art, a conflicting problem exists in that the raw material is preferably soft, but the hardness of the cutting blade must be increased in order to provide a satisfactory grinding ability. In order to solve such problem, the raw material of the hardness that satisfies both aspects is being used. However, in the present invention, the hardness of the cutting blade part 31*a* can be increased by forming the hardened layer 34. Thus, with regards to the raw material, the raw material that is softer than the raw material conventionally used is used, and an ideal root canal treatment instrument that preferably enhances both grinding ability and flexibility is realized.

The medical needle and the like according to the present invention is extremely effective in that the resistance when piercing, the resistance when scraping, and the resistance when incising the body tissue are reduced since the surface has high hardness, the difficult bending property is provided when having fiber shape structure, and further, the fatigue of the physicians when performing delicate surgery using microscope or endoscope is alleviated when the dark layer is formed on the surface to provide non-reflectivity.

What is claimed is:

1. A medical needle or a cutting tool comprising:
   (a) a fiber shave structure comprised of austenite stainless steel containing 1% to 6% of molybdenum or 13% to 25% of chromium, said structure having a surface;
   (b) a hardened layer disposed on/in the fiber shave structure, said hardened layer having been formed via a carburization process comprising placing the fiber shave structure in a carburizing gas atmosphere maintained at equal to or lower than 500° C., so as to cause penetration of carbon atoms into the surface of the fiber shave structure, and then removing some portion of the depth of the hardened layer, so as to form a hardened layer having a thickness of 5 micrometers to 70 micrometers;
   (c) a dark layer formed on an outer most surface of the hardened layer, said dark layer providing a non-reflective surface; and
   (d) a silicon coating formed on the dark layer.

2. The medical needle or cutting tool according to claim 1, wherein the silicon coating is formed after wiping a chromium carbide layer on an outer most surface of the dark layer.

\* \* \* \* \*